(12) United States Patent
Smith et al.

(10) Patent No.: US 6,451,775 B1
(45) Date of Patent: Sep. 17, 2002

(54) CASTOR AMIDOPROPYL DIMETHYL PHOSPHOLIPIDS AS EMULSIFIERS

(75) Inventors: Scott Smith, Chattanooga, TN (US); Dean Smith, Chattanooga, TN (US); Anthony J. O'Lenick, Jr., Dacula, GA (US)

(73) Assignee: Colonial Chemical Inc., South Pittsburg, TN (US)

( * ) Notice: Subject to any disclaimer, the term of this patent is extended or adjusted under 35 U.S.C. 154(b) by 0 days.

(21) Appl. No.: 09/940,942

(22) Filed: Aug. 29, 2001

(51) Int. Cl.7 .............................................. A61K 31/66
(52) U.S. Cl. ...................... 514/77; 558/169; 554/41; 424/59
(58) Field of Search ........................ 558/169; 554/41; 424/59; 514/77

(56) References Cited

U.S. PATENT DOCUMENTS 4,209,449 A * 6/1980 Mayhew et al.
4,503,002 A * 3/1985 Mayhew et al.
4,215,064 A * 7/1990 Lindemann et al.
6,331,293 B1 * 12/2001 Smith et al. .................. 424/59

OTHER PUBLICATIONS

CA:94:7595 abs EP 14509 Aug. 1980.*

CA:111:140203 abs of JP 63211208 Sep. 1988.*

CA:121:65281 abs of JP 06065053 Mar. 1994.*

* cited by examiner

*Primary Examiner*—Jean F. Vollano

(57) ABSTRACT

The present invention relates to novel compounds and, more particularly, to a class of compounds having specific quatenized amine based upon a castor amido amine linked to specific phosphate esters. Castor oil contains predominantly ricinoleic moieties. This phospholipid is an excellent emulsifier, conditioner and provides foam in formulations. It is also substantitive to human skin and is well tolerated by human tissue making it suitable for use in personal care applications.

4 Claims, No Drawings

CASTOR AMIDOPROPYL DIMETHYL PHOSPHOLIPIDS AS EMULSIFIERS

FIELD OF THE INVENTION

The present invention relates to novel compositions and, more particularly, to a class of compounds having specific quaternized amine based upon a castor amido amine linked to specific phosphate esters. Castor is an oil that contains a high quantity of a hydroxy containing C-18 having unsaturation present in the group. This allows for the synthesis of a phospholipid composition, which has outstanding emulsification properties and is liquid and surprisingly water-soluble. In addition this material is not toxic to human skin and is well tolerated by human tissue making it suitable for use in the preparation products for personal care applications.

BACKGROUND OF THE INVENTION

Phosphate ester and quaternary amine compounds are well known and have been widely used for many years. More recently, various betaine-type derivatives having, in general, quaternized alkyl amine groups and at least one phosphorous-containing anion in the molecule referred to hereinafter as "synthetic phospholipids", have been disclosed. The U.S. Pat. Nos. are 3,856,893 and 3,928,509 to Diery et al. Diery discloses that the phosphonate compounds of his invention are active anti-microbial compounds. Later amdido amine and imidazoline derivatives were disclosed for example, in U.S. Pat. Nos. 4,215,064; 4,233,192 and 4,380,637 to Lindemann et al., U.S. Pat. Nos. 4,209,449; 4,336,385 and 4,503,002 to Mayhew et al., and U.S. Pat. Nos. 4,243,602; 4,283,542 and 4,336,386 to O'enick et al. These synthetic phospholipids are suggested as exhibiting an outstanding combination of surfactant characteristics as well as being well tolerated by human tissue, i.e., they exhibit exceptionally low ocular irritation and oral toxicity. While these known phospholipids have been found useful as surfactants in a variety of personal care, they have not exhibited an ability to protect the skin from irritation or provide barrier properties to the skin, protecting it from the negative effects of chemicals and environmental effects.

It is very desirable to provide a material from aqueous solution that will protect the skin from environmental irritants such as ozone, and other pollutants. The compounds of the present invention can be formulated into body washes and other skin products and protect the skin from damage. In addition the di-nature of the compounds provides for outstanding substantivity and the phospholipid nature of the molecule allow for very mild natural like materials that can be used in products where low irritation is important.

SUMMARY OF THE INVENTION

Objective of the Invention

It is the objective of the invention to provide a novel castor based phospholipid and a process of its use which comprises using it as an emulsifier and conditioner in personal care applications.

In accordance with the present invention we have now been discovered novel phospholipid compound, which conform to the following structure:

$$R\text{---}C(O)\text{---}N(H)\text{---}(CH_2)_3\text{---}N^+\begin{array}{c}CH_3\\ \diagup\\ \diagdown\\ CH_3\end{array}\text{---}CH_2CH(OH)CH_2\text{---}OP(O)\text{---}O^-\quad O^-Na^+$$

wherein;

R is ricinoleic.

The present invention is directed toward a process for conditioning skin that comprises contacting the skin with an effective conditioning amount of a phospholipid compound, which conforms to the following structure:

$$R\text{---}C(O)\text{---}N(H)\text{---}(CH_2)_3\text{---}N^+\begin{array}{c}CH_3\\ \diagup\\ \diagdown\\ CH_3\end{array}\text{---}CH_2CH(OH)CH_2\text{---}OP(O)\text{---}O^-\quad O^-Na^+$$

wherein;

R is the ricinoleic moiety conforming to the following structure $$-(CH_2)_7-CH=CH-CH_2CH(OH)(CH_2)_5CH_3.$$

The effective conditioning concentration ranges from 0.1% to 15% by weight of the phospholipid. In a preferred embodiment the effective conditioning concentration ranges from 1.0% to 5% by weight of the phospholipid.

Preferred Embodiments

In a preferred embodiment the effective emulsifying concentration ranges from 0.5% to 25% by weight with 3 to 15% being the preferred concentration.

In another preferred embodiment the emulsions contain an anionic surfactant selected from the group consisting of alcohol sulfates. Alcohol ether sulfates and alpha olefin sulfonate.

In still another preferred embodiment the emulsions contain a non-ionic surfactant selected from the group consisting of alkanolamids, and fatty alcohol ethoxylated.

DETAILED DESCRIPTION OF THE INVENTION

The present invention is directed to novel phospholipid compounds, which conform to the following structure:

$$R\text{---}C(O)\text{---}N(H)\text{---}(CH_2)_3\text{---}N^+\begin{array}{c}CH_3\\ \diagup\\ \diagdown\\ CH_3\end{array}\text{---}CH_2CH(OH)CH_2\text{---}OP(O)\text{---}O^-\quad O^-Na^+$$

wherein;

R is ricinoleic which is —$(CH_2)_7$—CH=CH—$CH_2$CH(OH)$(CH_2)_5CH_3$.

The compounds of the present invention are prepared by reacting first reacting castor with dimethylaminopropyl amine (DMAPA) to give a tertiary amine intermediate.

$$R\text{—}C(O)\text{—}OH + 2\,H_2N\text{—}(CH_2)_3N\begin{array}{c}CH_3\\ |\\ |\\ CH_3\end{array}\quad\xrightarrow{-H_2O}$$

-continued $$R-C(O)-N(H)-(CH_2)_3-N\begin{matrix}CH_3\\ \\CH_3\end{matrix}$$

Ricinoleylamido-amine

This intermediate is then reacted with 3-chloro-2hydroxypropyl-phosphate made in accordance with the procedure outlined in U.S. Pat. No. 4,283,542 to O'Lenick, incorporated herein by reference.

$$R-C(O)C(O)-N(H)-(CH_2)_3-N\begin{matrix}CH_3\\ \\CH_3\end{matrix} +$$

$$2 \quad Cl-CH_2-CH(OH)CH_2-O-P(O)-(O\,Na)_2$$

3-chloro-2hydroxypropyl-phosphate disodium salt $$R-C(O)-N(H)-(CH_2)_3-N^+\begin{matrix}CH_3\\ \\CH_3\end{matrix}-CH_2CH(OH)CH_2-OP(O)-O^-\\ \quad\quad\quad\quad\quad\quad\quad\quad\quad\quad\quad\quad\quad\quad\quad\quad\quad\quad\quad\quad\quad\quad\quad\quad\quad\quad\quad | \\ \quad\quad\quad\quad\quad\quad\quad\quad\quad\quad\quad\quad\quad\quad\quad\quad\quad\quad\quad\quad\quad\quad\quad\quad\quad\quad O^-Na^+$$

wherein;

R is ricinoleic.

The compounds of the present invention are made reaction of the intermediate above with the dimmer diamidoamine under aqueous conditions. The product of the invention is thereby attained.

The compatibility of this novel phospholipid compounds of the invention with human tissue, i.e., dermal and eye tissue has also been tested. In these tests, 48-hour human patch dermal evaluations (5% in water), in vitro ocular evaluations (3% in water) and repeated insult patch tests (3% in water) determined that the compounds are substantially non-irritating to humans, they are safe and suitable for use in eye area products and are not a skin sensitizer to humans.

EXAMPLES

Castor oil and ricinoleic acid are items of commerce commercially available from several suppliers, one of which is The Fanning Corporation Chicago Ill.

Dimethyl aminopropyl Amine is an item of commerce available from a variety of sources including Dow Chemical.

Epichlorohydrin is an item of commerce available from a variety of sources including Dow Chemical.

Disodium phosphate is an item of commerce available from a variety of sources.

Example 1

Preparation of Castor Amido Amine

To 300.0 grams if castor is added 153.0 grams of dimethylaminopropyl amine. The mixture is heated to 180–200° C. and held for 3–8 hours. Once the temperature begins to reach 180 C. water begins to distill off. An excess of dimethylaminopropyl amine is added to speed up the reaction. When the acid value reaches 1.0 mg KOH/gram the excess dimethylaminopropyl amine is stripped off by applying vacuum. The resulting product is the dimer amido amine useful as an intermediate in the preparation of the compounds of the present invention. The alkali value of the product so produced is 180.0 mg KOH/gm. The product is a yellow water insoluble liquid at ambient temperatures.

Example 2

Preparation of 3-chloro-2-hydroxypropyl phosphate Intermediate

To a suitable reaction vessel equipped with reflux condenser, thermometer and agitation is added 142.0 grams of $Na_2PO_4$ and 424.5 grams of de-ionize water. Mix well until a solution is obtained. Next add 141.0 grams of Epichlorohydrin under agitation. Apply heat to 90 C., refluxing back into the vessel any distillate. As the temperature increases to 95–100 C. the contents will clear. Hold at this temperature for 3–4 hours. The resulting product is a 40%v aqueous solution of;

$$Cl-CH_2-CH(OH)CH_2-O-P(O)-(O\,Na)_2$$

Example 3

Preparation of the Phospholipid of the Present Invention

Into a suitable reaction flask is charged 937.0 grams of de-ionized water. An aqueous solution of 652.0 grams of 3-chloro-2-hydroxypropyl phosphates Intermediate (Example 2) is next added into the reaction vessel. Heat is applied to 90° C. Next, 625.0 grams of dimer amidoamine (example 1) are charged into the reaction vessel under good agitation. The temperature is maintained at between 90° C. and 95° C., until the percentage of free tertiary amine is 0.5% maximum. During the reaction time the pH is kept at between 7 and 8 with NaOH as required. The reaction mass will clear when the product is at 90 C. for about 1 hour. The reaction time is approximately 6 to 9 hours. The % NaCl is monitored and the reaction is deemed complete when the % of theoretical NaCl reaches 98%.

The compound of the present invention is used without additional purification. It is a clear viscous liquid and is sold as an aqueous solution of between 30 and 40% solids by weight. Unlike other phospholipids having eighteen carbon atoms in the hydrophobe, the presence of the hydroxyl group allows for the preparation of compounds that do not require a co-solvent like propylene glycol.

APPLICATIONS

The compounds of the present invention can be used to make emulsions that are surprisingly stable. Lecithin is a material that is very easily emulsified with the compound of the present invention. Emulsions prepared using this compound are not sticky on the skin. It appears that the product that remains on the skin has an affinity for the skin and protects the skin from the defatting effects of surfactants known to remove skin lipids.

Keeping skin lipids on the skin and preventing their removal by environmental pollution and chemicals is a major way that akin can be kept healthy. The balance of water, lipids and other natural chemicals need to be kept in balance for the skin to be healthy and have a good appearance.

The compounds of this invention are mildly substantive to the skin and protect the skin from water loss and maintain the natural balance of oil to water in the skin. The barrier allows for air to pass into the skin surface, but retards the loss of natural skin moisture. This results in skin that is dry and flaky.

While not wanting to be held to a specific scientific principle, one possible reason for the unexpected and beneficial effects of the compounds of the present invention is that the relatively high molecular weight as well as the affinity of the molecule for natural phospholipid materials results in a bond. The concept is simply "like dissolves like", or more specifically, like associates with like to give an overall system favored thermodynamically.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A phospholipid compound, which conforms to the following structure:

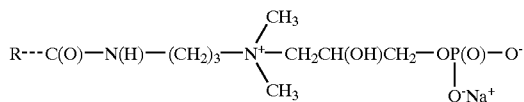

wherein;

R is —(CH$_2$)$_7$—CH=CH—CH$_2$CH(OH)(CH$_2$)$_5$CH$_3$.

2. A process for conditioning skin, which comprises contacting the skin with an effective conditioning amount of a phospholipid compound, which conforms to the following structure:

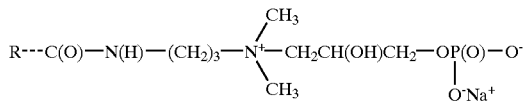

wherein;

R is —(CH$_2$)$_7$—CH=CH—CH$_2$CH(OH)(CH$_2$)$_5$CH$_3$.

3. A process of claim 2 wherein said effective conditioning concentration ranges from 0.1% to 15% by weight of the phospholipid.

4. A process of claim 2 wherein said effective conditioning concentration ranges from 1.0% to 5% by weight of the phospholipid.

* * * * *